(12) United States Patent
Flanagan et al.

(10) Patent No.: US 11,812,926 B2
(45) Date of Patent: Nov. 14, 2023

(54) MEDICAL DEVICE TRACKING SYSTEMS AND METHODS OF USING THE SAME

(71) Applicant: Boston Scientific Scimed, Inc., Maple Grove, MN (US)

(72) Inventors: Aiden Flanagan, Kilcolgan (IE); Bryan Clark, Forest Lake, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 387 days.

(21) Appl. No.: 17/109,933

(22) Filed: Dec. 2, 2020

(65) Prior Publication Data

US 2021/0161361 A1    Jun. 3, 2021

Related U.S. Application Data

(60) Provisional application No. 62/942,959, filed on Dec. 3, 2019.

(51) Int. Cl.
| | |
|---|---|
| *A61B 1/00* | (2006.01) |
| *A61B 34/20* | (2016.01) |
| *A61B 1/005* | (2006.01) |
| *A61B 1/018* | (2006.01) |
| *A61B 1/05* | (2006.01) |
| *A61B 1/06* | (2006.01) |

(52) U.S. Cl.
CPC .... *A61B 1/000096* (2022.02); *A61B 1/00006* (2013.01); *A61B 1/0057* (2013.01); *A61B 1/018* (2013.01); *A61B 1/05* (2013.01); *A61B 1/063* (2013.01); *A61B 1/0661* (2013.01); *A61B 34/20* (2016.02)

(58) Field of Classification Search
CPC .............. A61B 1/000096; A61B 34/20; A61B 1/00006; A61B 1/0057; A61B 1/018; A61B 1/05; A61B 1/063; A61B 1/0661; A61B 34/30; A61B 1/00172; A61B 1/06; A61B 1/00017; A61B 2034/2055; A61B 2034/2059; A61B 2034/2065; A61B 2034/2068
USPC ........................................ 600/146; 356/622
See application file for complete search history.

(56) References Cited

U.S. PATENT DOCUMENTS

| | | | |
|---|---|---|---|
| 6,239,868 B1 * | 5/2001 | Jung | ......................... G01J 3/51 356/600 |
| 8,536,859 B2 | 9/2013 | Bar-Tal et al. | |
| 2008/0287783 A1 | 11/2008 | Anderson | |

(Continued)

OTHER PUBLICATIONS

International Search Report and Written Opinion in International Application No. PCT/US2020/062911, dated Feb. 18, 2021 (13 pages).

*Primary Examiner* — Timothy J Neal
*Assistant Examiner* — James Edward Boice
(74) *Attorney, Agent, or Firm* — Bookoff McAndrews, PLLC

(57) ABSTRACT

A medical system that includes a medical device having an imaging device configured to capture images of a target site. A location of the target site is determined based on the images. The medical device includes a light source configured to direct light onto the location of the target site, and a processor and non-transitory computer readable medium storing instructions that, when executed by the processor, causes the processor to move a sensor of a medical instrument toward the location of the target site based on the sensor detecting the light at the target site.

20 Claims, 5 Drawing Sheets

(56) References Cited

U.S. PATENT DOCUMENTS

| | | |
|---|---|---|
| 2009/0021818 A1 | 1/2009 | Weir et al. |
| 2011/0007327 A1 | 1/2011 | Bridges et al. |
| 2011/0015533 A1 | 1/2011 | Cox et al. |
| 2012/0123212 A1* | 5/2012 | Dahmen ............. A61B 1/0627 |
| | | 600/178 |
| 2012/0130171 A1* | 5/2012 | Barak ............... A61B 1/00009 |
| | | 600/117 |
| 2013/0023760 A1* | 1/2013 | Liu .................... A61B 5/0084 |
| | | 600/425 |
| 2013/0345510 A1 | 12/2013 | Hadani |
| 2014/0221748 A1 | 8/2014 | Kikuchi et al. |
| 2015/0078615 A1* | 3/2015 | Staples, II ............... G06T 7/50 |
| | | 382/103 |
| 2015/0181185 A1 | 6/2015 | Ikemoto et al. |
| 2016/0331473 A1* | 11/2016 | Yamamura ............ A61B 1/005 |
| 2018/0014851 A1* | 1/2018 | Hansen ............. A61B 17/3423 |
| 2018/0344288 A1 | 12/2018 | Ho et al. |

\* cited by examiner

MEDICAL DEVICE TRACKING SYSTEMS AND METHODS OF USING THE SAME

CROSS-REFERENCE TO RELATED APPLICATIONS

This application claims the benefit of priority from U.S. Provisional Application No. 62/942,959, filed Dec. 3, 2019, which is incorporated by reference herein in its entirety.

TECHNICAL FIELD

Various aspects of the disclosure relate generally to medical device tracking systems, devices, and related methods. More specifically, at least certain embodiments of the disclosure relate to systems, devices, and related methods for locating one or more target sites within a patient during an endoscopic procedure to facilitate the positioning of medical devices, among other aspects.

BACKGROUND

Technological developments have given users of medical systems, devices, and methods, the ability to conduct increasingly complex procedures on subjects. One challenge in the field of minimally invasive surgeries such as endoscopy, among other surgical procedures, is associated with the cannulation of target sites within a patient, such as an ampulla opening into the common bile duct. Placement of medical devices within a patient at precise locations of target sites may be difficult due to general lack of visualization at the target site and lack of control over a positioning of the medical device at a location of the target site. The limitations of medical devices in providing stability toward positioning an endoscope at a target treatment site of a patient may prolong the procedure, limit its effectiveness, and/or cause injury to the patient due to misalignment or instability of the medical device. There is a need for devices and methods that address one or more of these difficulties or other related problems.

SUMMARY

Aspects of the disclosure relate to, among other things, systems, devices, and methods for positioning a medical device at a target treatment site with a medical system including target identification logic, among other aspects. Each of the aspects disclosed herein may include one or more of the features described in connection with any of the other disclosed aspects.

According to an example, a medical system includes a medical device having an imaging device configured to capture images of a target site. A location of the target site is determined based on the images. The medical device further includes a light source configured to direct light onto the location of the target site, and a processor and non-transitory computer readable medium storing instructions that, when executed by the processor, causes the processor to move a sensor of a medical instrument toward the location of the target site based on the sensor detecting the light at the target site.

Any of the medical systems described herein may have any of the following features. The sensor is movable relative to the imaging device toward the location of the target site based on the sensor detecting the light at the target site. The instructions stored in the non-transitory computer readable medium causes the processor to detect a change in location of the imaging device relative to the target site, determine the location of the target site relative to the imaging device, and redirect the light to the location of the target site. The processor is configured to detect the change in location of the imaging device relative to the target site based on images periodically captured by the imaging device. The processor is configured to compare the location of the target site to an original location of the target site to determine a positional variance. The processor is configured to determine whether the positional variance exceeds a preprogrammed threshold. The light source includes a source to generate a laser beam. The imaging device includes a camera. The medical system may include a medical instrument, and wherein the sensor includes at least one of a photodetector, a photodiode, and a charged coupled device (CCD). The sensor is configured to generate a photodiode signal in response to detecting the light at the target site. A strength of the photodiode signal generated by the sensor includes a greater intensity when the sensor is positioned at a first distance from the light, and includes a smaller intensity when the sensor is positioned at a second distance from the light. The first distance is less than the second distance. The medical device includes a mirror configured to reflect the light generated by the light source toward the location of the target site. The mirror is configured to move to redirect the light toward the location of the target site in response to the processor detecting the change in location of the imaging device relative to the target site. The mirror includes a micro-mirror (MEMs mirror) configured to reflect the light along two axes. The mirror is positioned adjacent to the light source on the medical device. The processor is configured to generate a visual identifier along the images captured by the imaging device indicative of the location of the target site.

According to another example, a medical system includes a medical device including an imaging device configured to capture images of a target site, and a light source configured to direct light onto the target site. The medical system includes a medical instrument movable relative to the medical device. The medical instrument including a sensor configured to detect the light on the target site. The medical instrument is movable toward the target site in response to the sensor detecting the light on the target site.

Any of the medical systems described herein may have any of the following features. The medical system may include a processor configured to detect movement of the medical device relative to the target site based on images captured by the imaging device. The light source is configured to redirect the light based on the detected movement of the medical device. The medical device is an endoscope or duodenoscope, and the medical instrument is a catheter.

According to another example, a method of moving a medical instrument toward a target site includes capturing images of the target site with an imaging device. A first location of the target site is determined based on the images. The method includes transmitting light to the first location by a light source, detecting the light incident at the first location by a sensor of the medical instrument, and moving the medical instrument toward the target site based on the sensor detecting the light incident at the first location.

Any of the methods of using the medical systems described herein may have any of the following steps and/or features. In response to detecting movement of the medical device within the target site, the method includes capturing images of the target site with the imaging device to determine a second location of the target site, redirecting the light from the light source to the second location, and moving the medical instrument toward the target site based on the sensor detecting the light at the second location.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary aspects of the disclosure and together with the description, serve to explain the principles of the disclosure.

DETAILED DESCRIPTION

Embodiments of the disclosure include systems, devices, and methods for locating, tracking, and/or steering one or more tools or other medical devices at a target site within the body. Reference will now be made in detail to aspects of the disclosure, examples of which are illustrated in the accompanying drawings. Wherever possible, the same or similar reference numbers will be used through the drawings to refer to the same or like parts. The term "distal" refers to a portion farthest away from a user when introducing a device into a patient. By contrast, the term "proximal" refers to a portion closest to the user when placing the device into the patient. As used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal." As used herein, the terms "about," "substantially," and "approximately," indicate a range of values within +/−10% of a stated value.

Embodiments of the disclosure may be used to locate a target site with a medical system, such as, for example, a medical system having target identification logic. For example, some embodiments combine an imaging device and a light source with a medical device to locate a target site. The imaging device may capture images of the target site and the light source may direct light onto the target site in response to identifying a location of the target site based on the images. The target identification logic of the medical system may detect movements of the medical device and determine an adjusted location of the target site relative to the medical device in response, thereby redirecting the light from the light source toward the location of the target site.

Embodiments of the disclosure may relate to devices and methods for performing various medical procedures and/or treating portions of the large intestine (colon), small intestine, cecum, esophagus, any other portion of the gastrointestinal tract, and/or any other suitable patient anatomy (collectively referred to herein as a "target treatment site"). Various embodiments described herein include single-use or disposable medical devices. Reference will now be made in detail to examples of the disclosure described above and illustrated in the accompanying drawings. Wherever possible, the same reference numbers will be used throughout the drawings to refer to the same or like parts.

Figure 1:
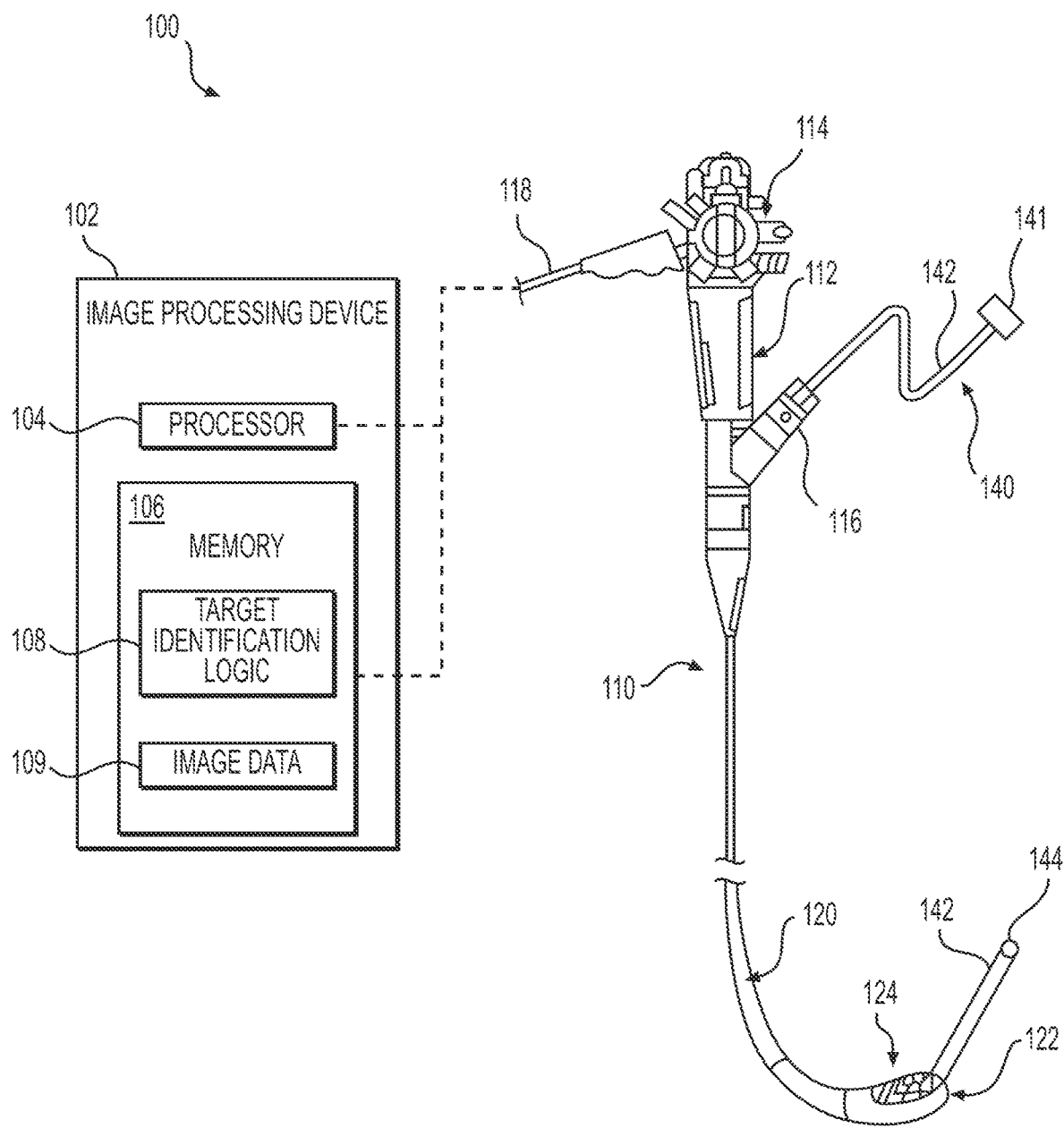
FIG. 1 is a schematic view of an exemplary medical system, according to aspects of this disclosure.

FIG. 1 shows a schematic depiction of an exemplary medical system 100 in accordance with an embodiment of this disclosure. The medical system 100 may include an image processing device 102, a medical device 110, and a medical instrument 140. The image processing device 102 may be communicatively coupled to the medical device 110 via a cable 118. It should be understood that in other embodiments the image processing device 102 may be in wireless communication with the medical device 110. In embodiments, the image processing device 102 is a computer system incorporating a plurality of hardware components that allow the image processing device 102 to receive and monitor data, accurately display images of one or more features (e.g., a target site), and/or process other information described herein. Illustrative hardware components of the image processing device 102 may include at least one processor 104 and at least one memory 106.

The processor 104 of the image processing device 102 may include any computing device capable of executing machine-readable instructions, which may be stored on a non-transitory computer-readable medium, such as, for example, the memory 106 of the image processing device 102. By way of example, the processor 104 may include a controller, an integrated circuit, a microchip, a computer, and/or any other computer processing unit operable to perform calculations and logic operations required to execute a program. As described in greater detail herein, the processor 104 is configured to perform one or more operations in accordance with the instructions stored on the memory 106, such as, for example, a target identification logic 108.

The memory 106 of the image processing device 102 is a non-transitory computer readable medium that stores machine-readable instructions thereon, such as, for example, the target identification logic 108. As described in further detail below, the target identification logic 108 may include executable instructions that allow the medical device 110 to track a location of a target site for the medical instrument 140 to lock onto and steer toward for the performance of one or more procedures on or near the target site. It should be understood that various programming algorithms and data that support an operation of the medical system 100 may reside in whole or in part in the memory 106. The memory 106 may include any type of computer readable medium suitable for storing data and algorithms, such as, for example, random access memory (RAM), read only memory (ROM), a flash memory, a hard drive, and/or any device capable of storing machine-readable instructions. The memory 106 may include one or more data sets, including, but not limited to, image data 109 from one or more components of the medical system 100 (e.g., the medical device 110, the medical instrument 140, etc.).

Still referring to FIG. 1, the medical device 110 may be configured to facilitate positioning one or more components of the medical system 100 relative to a patient, such as, for example, the medical instrument 140. In embodiments, the medical device 110 may be any type of endoscope and may include a handle 112, an actuation mechanism 114, at least one port 116, and a shaft 120. The handle 112 of the medical device 110 may have one or more lumens (not shown) that communicate with a lumen(s) of one or more other components of the medical system 100. The handle 112 further includes the at least one port 116 that opens into the one or more lumens of the handle 112. As described in further detail herein, the at least one port 116 is sized and shaped to receive one or more instruments therethrough, such as, for example, the medical instrument 140 of the medical system 100.

The shaft 120 of the medical device 110 may include a tube that is sufficiently flexible such that the shaft 120 is configured to selectively bend, rotate, and/or twist when being inserted into and/or through a patient's tortuous anatomy to a target treatment site. The shaft 120 may have one or more lumens (not shown) extending therethrough that include, for example, a working lumen for receiving instruments (e.g., the medical instrument 140). In other embodiments, the shaft 120 may include additional lumens such as a control wire lumen for receiving one or more control wires for actuating one or more distal parts/tools (including an articulation joint and an elevator, for example), a fluid lumen for delivering a fluid, an illumination lumen for receiving at least a portion of an illumination assembly (not shown), and/or an imaging lumen for receiving at least a portion of an imaging assembly (not shown).

Still referring to FIG. 1, the medical device 110 may further include a tip 122 at a distal end of the shaft 120. In some embodiments, the tip 122 may be attached to the distal end of the shaft 120, while in other embodiments the tip 122 may be integral with the shaft 120. For example, the tip 122 may include a cap configured to receive the distal end of the shaft 120 therein. The tip 122 may include one or more openings that are in communication with the one or more lumens of the shaft 120. For example, the tip 122 may include a working opening 124 through which the medical instrument 140 may exit from a working lumen of the shaft 120. In other embodiments, the tip 122 of the shaft 120 may include additional and/or fewer openings thereon, such as, for example, a fluid opening or nozzle through which fluid may be emitted from a fluid lumen of the shaft 120, an illumination opening/window through which light may be emitted, and/or an imaging opening/window for receiving light used by an imaging device to generate an image.

The actuation mechanism 114 of the medical device 110 is positioned on the handle 112 and may include one or more knobs, buttons, levers, switches, and/or other suitable actuators. The actuation mechanism 114 is configured to control at least one of deflection of the shaft 120 (through actuation of a control wire, for example), delivery of a fluid, emission of illumination, and/or various imaging functions. As described in greater detail herein, in some embodiments the medical device 110 includes one or more control wires for actuating an elevator 126 of the medical device 110 at the tip 122 (see FIGS. 2-3). Accordingly, a user of the medical device 110 may manipulate the actuation mechanism 114 to selectively exert at least one of a pulling force and a pushing force on the one or more control wires to control a position of the elevator 126, and thereby control a position of an instrument adjacent to the elevator 126 (e.g., the medical instrument 140).

Still referring to FIG. 1, the medical instrument 140 of the medical system 100 may include a catheter having a longitudinal body 142 between a proximal end of the longitudinal body 142 and a distal end 144. A handle 141 is at the proximal end of the longitudinal body 142. The longitudinal body 142 of the medical instrument is flexible such that the medical instrument 140 is configured to bend, rotate, and/or twist when being inserted into a working lumen of the medical device 110. The handle 141 of the medical instrument 140 may be configured to move, rotate, and bend the longitudinal body 142. Further, the handle 141 may define one or more ports (not shown) sized to receive one or more tools through the longitudinal body 142 of the medical instrument 140. The medical device 110 is configured to receive the medical instrument 140 via the at least one port 116 and through the shaft 120 to the working opening 124 at the tip 122 via a working lumen. In this instance, the medical instrument 140 may extend distally out of the working opening 124 and into a surrounding environment of the tip 122, such as, for example, at a target treatment site of a patient as described in further detail below. The distal end 144 of the medical instrument 140 may extend distally from the working opening 124 in response to a translation of the longitudinal body 142 through the working lumen of the shaft 120. It should be understood that in other embodiments the medical instrument 140 may include various other devices than those show and described herein, including but not limited to, a guidewire, cutting or grasping forceps, a biopsy device, a snare loop, an injection needle, a cutting blade, scissors, a retractable basket, a retrieval device, an ablation and/or electrophysiology catheter, a stent placement device, a surgical stapling device, a balloon catheter, a laser-emitting device, an imaging device, and/or any other suitable instrument.

Figure 2:
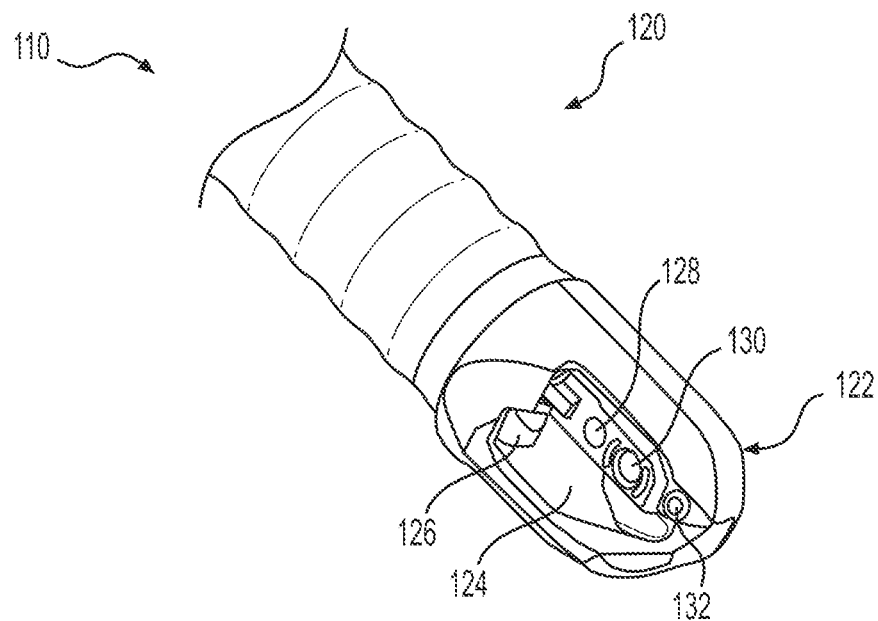
FIG. 2 is a partial perspective view of a medical device of the medical system of FIG. 1, according to aspects of this disclosure.

Referring now to FIG. 2, the tip 122 of the shaft 120 is depicted with the medical instrument 140 omitted from the working opening 124. The tip 122 includes the elevator 126 positioned adjacent to the working opening 124 and partially disposed within a working lumen of the shaft 120. It should be understood that the elevator 126 is shown and described herein in an unactuated position and that actuation of the actuation mechanism 114 on the handle 112 may provide for an extension of the elevator 126 to an actuated position (see FIG. 3). As described in further detail below, the elevator 126 is configured to position an instrument received through a working lumen of the shaft 120 (e.g., the medical instrument 140) outward from the working opening 124 when in the actuated position.

The tip 122 of the medical device 110 further includes a light source 128, an imaging device 130, and a laser 132 positioned adjacent to the working opening 124 of the shaft 120. In embodiments, the light source 128 of the medical device 110 is configured and operable to direct light outwardly from the tip 122 of the shaft 120 to thereby illuminate a surrounding environment of the tip 122, such as, for example, a target treatment site of a patient in which the medical device 110 may be located in (see FIGS. 5A-5C). The light source 128 may include a light emitter, such as, for example, a light-emitting diode (LED), or the like. The imaging device 130 of the medical device 110 is configured and operable to capture images of a surrounding environment of the tip 122, such as, for example, the target treatment site of a patient (see FIGS. 5A-5C). In some embodiments, the imaging device 130 may include a camera capable of high resolution imaging. It should be understood that in other embodiments the medical device 110 may omit the imaging device 130 on the tip 122 entirely such that a separate imaging device may be received by the medical device 110 through the shaft 120.

Still referring to FIG. 2, the laser 132 of the medical device 110 is configured and operable to generate a light/laser beam outwardly from the tip 122 of the shaft 120. In some embodiments, the laser 132 is further configured to selectively direct the light/laser beam to a predetermined location to thereby mark the predetermined location with the light/laser beam. It should be understood that the light/laser beam generated by the laser 132 may be independently steerable relative to the light emitted by the light source 128 and/or any other component of the medical system 100. As described further below, a target site within a patient may be marked with a light/laser beam from the laser 132 for tracking a location of said target site during use of the medical system 100 in a procedure (see FIGS. 5A-5C).

In some embodiments, the medical device 110 may further include a mirror positioned along and/or adjacent to the tip 122 of the shaft 120. The mirror of the medical device 110 may be disposed adjacent to the laser 132 thereby forming a unitary structure such that the mirror is coincident with a beam of light emitted by the laser 132. In embodiments, the mirror of the medical device 110 is configured and operable to selectively reflect the light/laser beam generated by the laser 132 toward a predetermined location of a target site. The mirror of the medical device 110 is configured to move, pivot, translate, and/or rotate relative to the laser 132 and/or the tip 122 of the shaft 120 to thereby redirect the light/laser beam to a predetermined location of the target site. In embodiments, the mirror includes a micromirror (MEMS mirror) configured to reflect the light/laser beam along two axes (e.g., x-y directions of a coordinate axis) and/or to optical scanning angles ranging up to approximately 32 degrees. As described in further detail below, a predetermined location of a target site may be determined based on images (e.g., the image data 109) captured by the imaging device 128 of the medical device 110.

Figure 3:
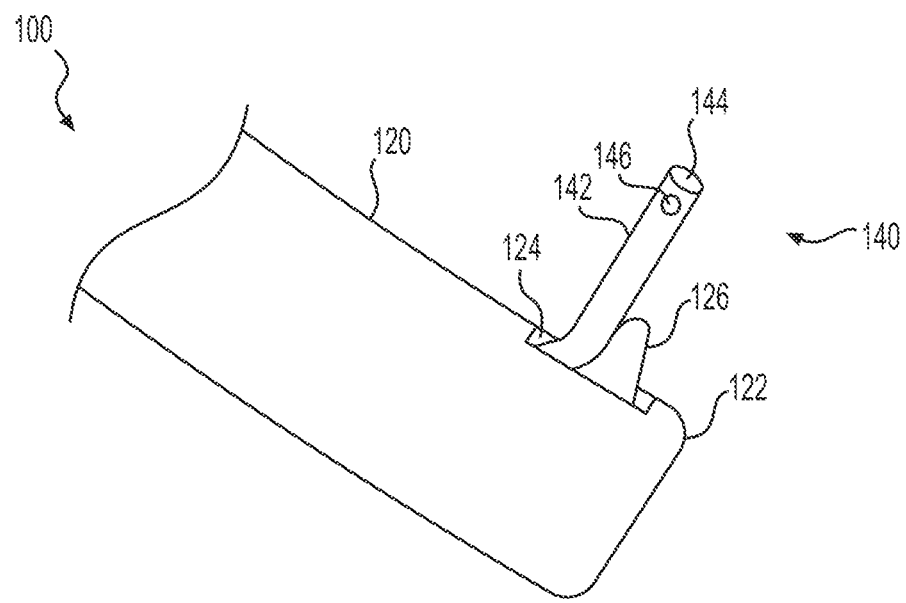
FIG. 3 is a partial perspective view of a medical instrument of the medical system of FIG. 1, according to aspects of this disclosure.

As shown in FIG. 3, the medical instrument 140 is depicted extending outwardly from the tip 122 of the shaft 120 with the elevator 126 engaged against the longitudinal body 142 of the medical instrument 140. With the elevator 126 in an actuated position, an anterior-facing surface of the elevator 126 engages the longitudinal body 142 of the medical instrument 140 to thereby deflect the distal end 144 laterally outward from the working opening 124. In some embodiments, the anterior-facing surface of the elevator 126 has a curvature that facilitates a deflection and/or bend of the longitudinal body 142 of the medical instrument 140. It should be appreciated that the elevator 126 may include various other shapes, sizes, and/or configurations than those shown and described herein without departing from a scope of the disclosure.

The medical instrument 140 further includes a sensor 146 positioned along the longitudinal body 142 adjacent to the distal end 144. In embodiments, the sensor 146 may be located on a distally-facing surface and/or a distal-most surface of the medical instrument 140. The sensor 146 of the medical instrument 140 is configured to detect one or more objects, properties, characteristics, and/or features present at and/or proximate to the distal end 144 of the medical instrument 140. By way of example, in some embodiments the sensor 146 may be configured to detect light, such as the light generated by the light source 128 of the medical device 110. In other embodiments, the sensor 146 may be configured to detect the light/laser beam generated by the laser 132 of the medical device 110, for example a point on a target site on which the light/laser beam 132 is incident. The sensor 146 may include at least one of a photodetector, a photodiode, a charged coupled device (CCD), and/or various other suitable detectors.

In embodiments, the sensor 146 includes a four-quadrant photodiode configured to convert light into an electrical current. As described in greater detail herein, in embodiments the sensor 146 is configured and operable to identify a predetermined location of a target site in response to detecting a light/laser beam directed by the laser 132 onto that target site (see FIGS. 5A-5C). In some embodiments, the sensor 146 may be positioned along a proximal end of the longitudinal body 142 adjacent to the handle 141 of the medical instrument 140 with a fiber that is communicatively coupled to the sensor 146 positioned adjacent to the distal end 144. In this instance, the distal end 144 of the medical instrument 140 may have a relatively smaller profile. It should be understood that in other embodiments the medical instrument 140 may omit the sensor 146 on the distal end 144 entirely such that a separate sensing device may be received by the medical instrument 140 through the longitudinal body 142, such as, for example, via one or more guidewires.

Figure 4:
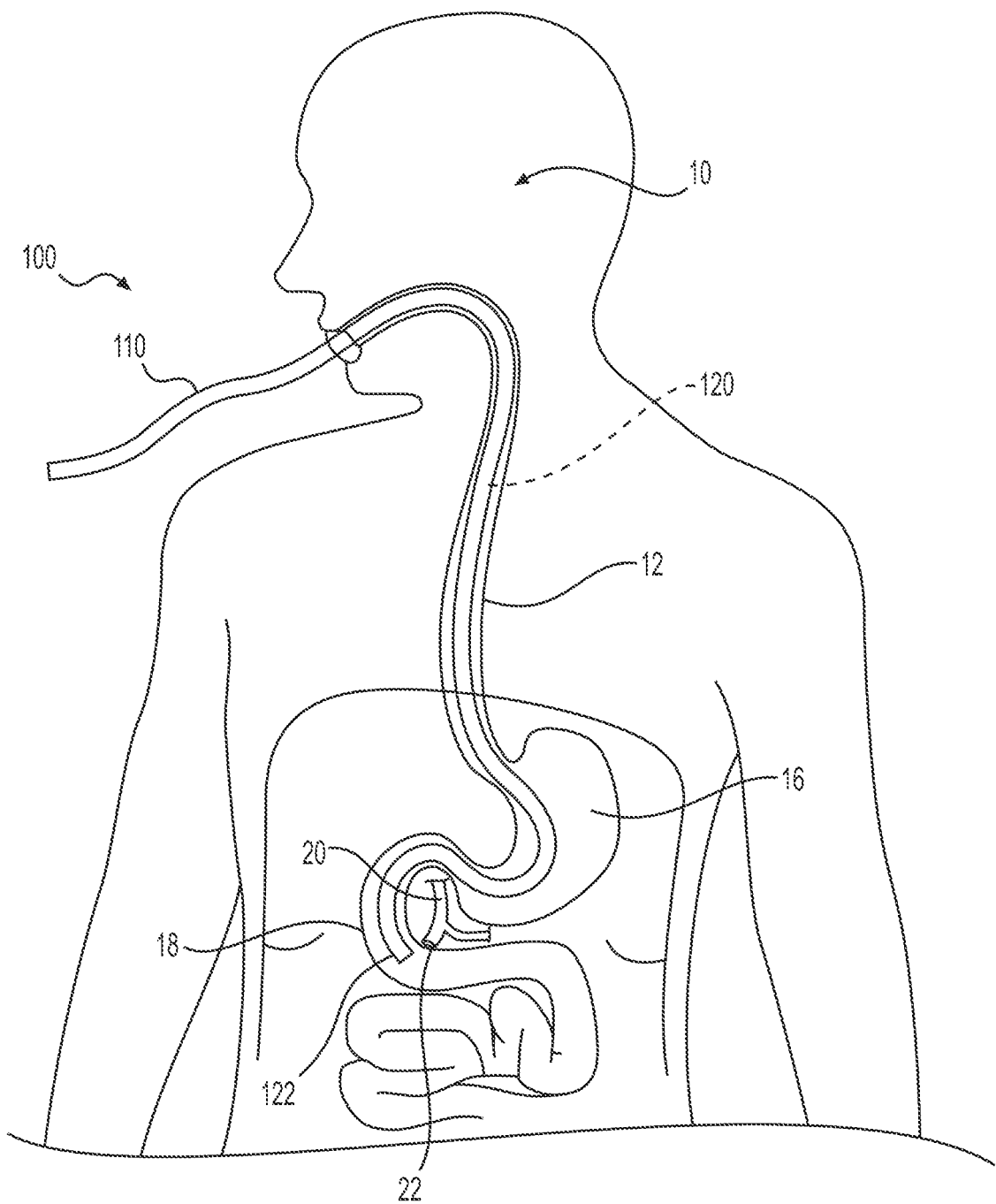
FIG. 4 is a schematic view of the medical system of FIG. 1 positioned at a target site of a patient, according to aspects of this disclosure.
Figure 5A:
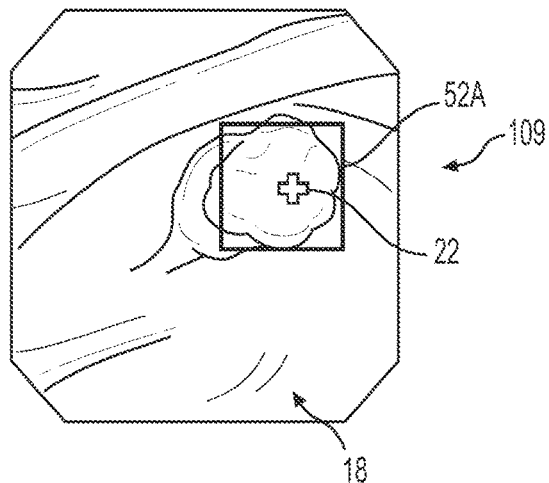
FIG. 5A is an image including locating a target site of a patient, according to aspects of this disclosure.
Figure 5B:
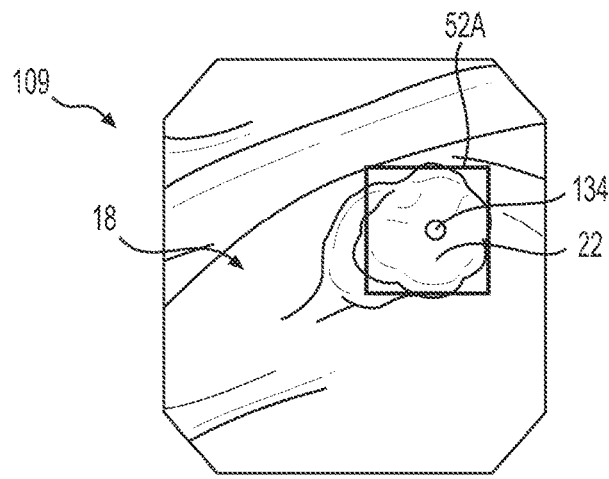
FIG. 5B is an image including marking the target site of FIG. 5A with a light beam, according to aspects of this disclosure.
Figure 5C:
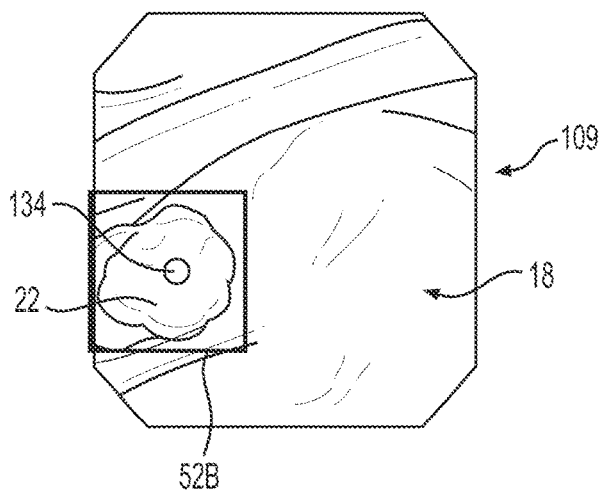
FIG. 5C is an image including marking a target site with a light beam upon movement of the medical system, according to aspects of this disclosure.
Figure 6:
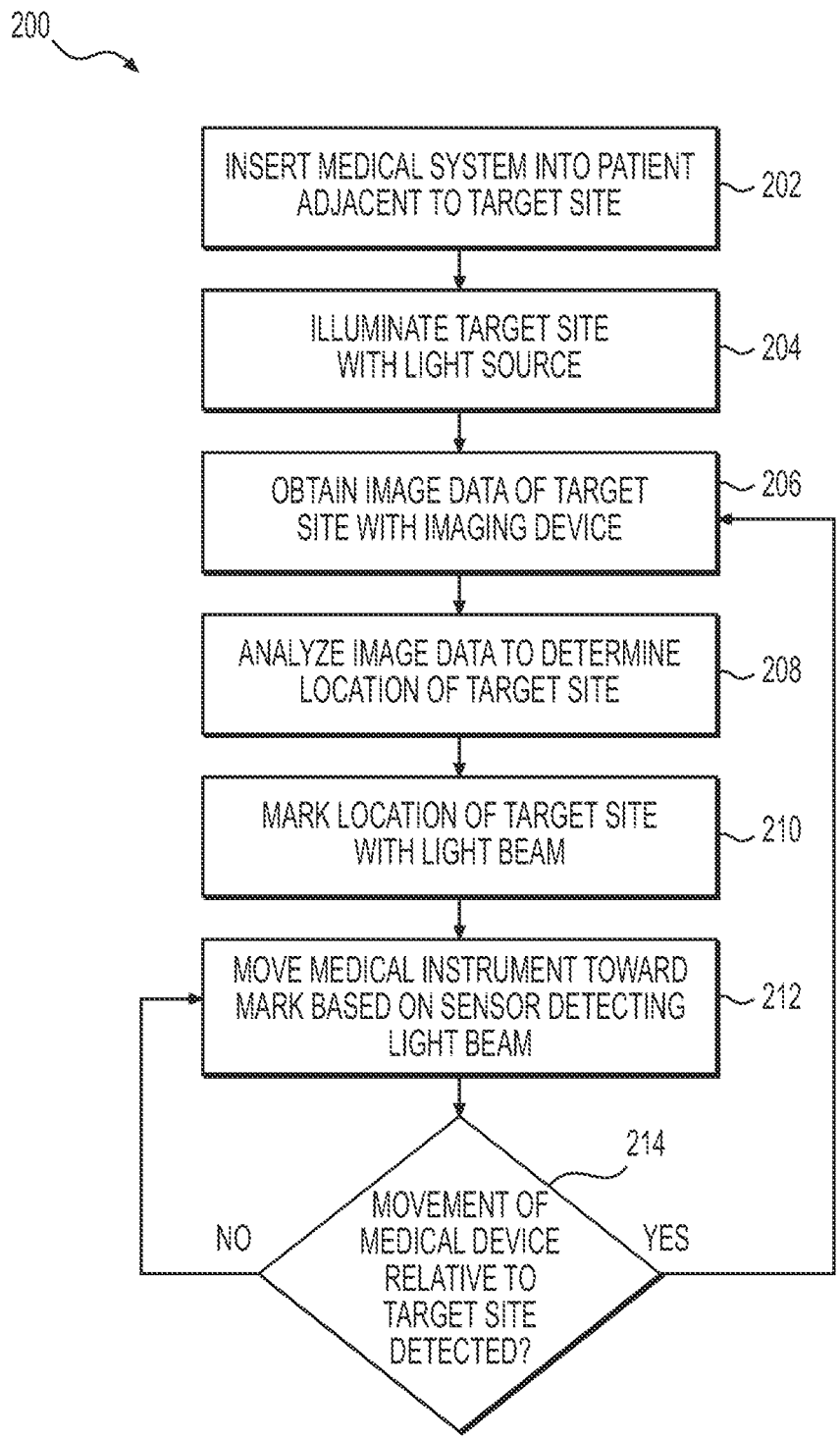
FIG. 6 is a block diagram of an exemplary method of locating a target site with the medical system of FIG. 1, according to aspects of this disclosure.

Referring now to FIGS. 4-5C in conjunction with the flow diagram of FIG. 6, an exemplary method 200 of using the medical system 100 to locate and access a target site is schematically depicted. The depiction of FIGS. 4-6 and the accompanying description below is not meant to limit the subject matter described herein to a particular method.

At step 202 and as shown in FIG. 4, the medical device 110 of the medical system 100 may be inserted within a patient's body 10. The shaft 120 of the medical device 100 is guided through a digestive tract of the patient 10 by inserting the tip 122 into a nose or mouth (or other suitable natural body orifice) of the patient's body 10. In embodiments, the medical device 110 is inserted through a gastrointestinal tract of the patient's body 10, including an esophagus 12, a stomach 16, and into a small intestine 18 until reaching a target treatment site. It should be appreciated that a length of the shaft 120 may be sufficient so that a proximal end of medical device 110 (including the handle 112) is external of the patient's body 10 while the tip 122 of the medical device 110 is internal to the patient's body 10. While this disclosure relates to the use of the medical system 100 in a digestive tract of the patient's body 10, it should be understood that the features of this disclosure could be used in various other locations (e.g., other organs, tissue, etc.) within the patient's body 10.

The shaft 120 of the medical device 110 may extend into the patient's body 10 until it reaches a position in which tools disposed within the medical device 110 can access the target treatment site, such as the medical instrument 140 of the medical system 100. In examples in which the medical device 110 is used to access and visualize aspects of the pancreatico-biliary system, this position may be, for example, the duodenum of the small intestine 18. In such examples, a target site may be the ampulla/papilla of Vater 22 located in a portion of the duodenum of the small intestine 18. It should be understood that the ampulla/papilla of Vater 22 generally forms an opening where the pancreatic duct and the common bile duct 20 empty into the duodenum of the small intestine 18, with the hepatic ducts and the gall bladder emptying into the common bile duct 20.

Still referring to FIG. 4, with the tip 122 of the shaft 120 located proximate to the target site (e.g., the ampulla of Vater 22), the medical instrument 140 of the medical system 100 may be slidably received within the medical device 110 to thereby position the distal end 144 proximate to the target site. Advancement of the medical instrument 140 into the port 106 and through the shaft 120 to the tip 122 may be provided in response to actuation of the handle 142. It should be understood that in other embodiments the medical instrument 140 may be received through the medical device 110 prior to an insertion of the shaft 120 through the patient body 10 at step 202.

In some embodiments, rotation of the tip 122 near the target site may be desirable to facilitate positioning the working opening 124 toward a location of the target site. For example, it may be desired that the distal end 144 of the medical instrument 140 reach the ampulla/papilla of Vater 22 when deflected outwardly from the working opening 124 by the elevator 126 (FIG. 3). In this instance, the tip 122 of the shaft 120 may be rotated until the working opening 124, in which the medical instrument 140 may exit the medical device 110, is facing the ampulla/papilla of Vater 22. Rotation of the tip 122 and/or the shaft 120 may be provided in response to actuating the actuation mechanism 114 on the handle 112, and/or by rotating all of the handle 112, and identification of a relative orientation and/or position of the tip 122 may be provided in response to actuating the imaging device 130 on the tip 122.

At step 204, with the working opening 124 on the tip 122 facing the target site, a surrounding environment of the target site may be illuminated in response to actuating the light source 128. It should be understood that in other embodiments the light source 128 may already be actuated to direct light outwardly from the tip 122, such as, for example, prior to and/or as the medical device 110 is inserted into the patient body 10 at step 202.

At step 206, with the target site illuminated by the lighting source 128, the processor 104 of the image processing device 102 executes the target identification logic 108 to actuate the imaging device 130 of the medical device 110. Accordingly, the imaging device 130 captures images of the target site. With the imaging device 130 facing the target site (e.g., the ampulla of Vater 22), images of a location of the target site may be obtained by the medical device 110 and communicated to the image processing device 102 for storing in the memory 106 as image data 109.

At step 208 and referring to FIG. 5A, with the image data 109 received from the medical device 110 and stored within the memory 106, the processor 104 of the image processing device 102 executes the target identification logic 108 to determine a first location 52A of the target site (e.g., the ampulla of Vater 22 within the small intestine 18) relative to the imaging device 130 on the tip 122. The processor 104 analyzes the image data 109 captured by the imaging device 130 and determines a coordinate position of the target site relative to the tip 122, pursuant to executing the machine-readable instructions of the target identification logic 108. Alternatively, in other embodiments a user of the medical system 100 may manually identify the first location 52A of the target site based on the image data 109, such as, for example, via a touch-screen user interface display (not shown) that is communicatively coupled to the image processing device 102.

In some embodiments, the processor 104, when executing the target identification logic 108, may generate a visual identifier at the first location 52A (e.g., highlights, geometric figures, arrows, and the like) to thereby visually designate the first location 52A of the target site for reference. As seen in FIG. 5A, the visual identifier of the first location 52A may include a box and/or "X" superimposed on the images of the target site for purposes of visually designating the target site in the image data 109. The visual identifier of the first location 52A may be displayed on a user interface display (not shown) that is communicatively coupled to the image processing device 102. Alternatively, in other embodiments a user of the medical system 100 may manually mark the first location 52A of the target site with a visual identifier based on the image data 109, such as, for example, via a touch-screen user interface display (not shown) that is communicatively coupled to the image processing device 102. In this instance, the processor 104 may analyze the image data 109 to determine the first location 52A of the target site in accordance with the manual mark and/or identification by the user of the medical system 100 for continued tracking in subsequent images of the target site.

At step 210 and referring to FIG. 5B, with the first location 52A of the target site determined relative to the tip 122, the processor 104 of the image processing device 102 executes the target identification logic 108 to mark the first location 52A of the target site with a light/laser beam 134 by actuating the laser 132 of the medical device 110. The processor 104 actuates the mirror of the medical device 110 to reflect the light/laser beam 134 generated by the laser 132 to redirect the light/laser beam 132 toward the first location 52A of the target site, pursuant to executing the machine-readable instructions of the target identification logic 108.

At step 212 and still referring to FIG. 5B, with the light/laser beam 134 of the laser 132 directed (e.g., by the mirror) to the first location 52A of the target site (e.g., the ampulla of Vater 22), the medical instrument 140 may be moved toward the target site in response to sensor 146 detecting the light/laser beam 132. The handle 141 of the medical instrument 140 may be actuated to automatically translate the longitudinal body 142 through a working lumen of the shaft 120 to position the distal end 144 adjacent to the target site. Accordingly, the medical device 110 tracks the first location 52A of the target site to allow the medical instrument 140 to lock onto the first location 52A with the sensor 146 and autonomously steer the distal end 144 toward the target site to perform one or more procedures thereon, such as, for example, cannulate the ampulla duct opening 22 of the common bile duct 20.

With the sensor 146 positioned along the distal end 144, the sensor 146 is configured to generate a feedback in response to detecting the incidence of the light/laser beam 132 onto the target site, relative to the distal end 144. In some embodiments, the sensor 146 includes a photodiode configured to convert the light/laser beam 134 into an electrical current such that the feedback generated by the sensor 146 includes a photodiode signal transmitted to a user of the medical instrument 140. A strength of the photodiode signal generated by the sensor 146 may be indicative of a spatial (e.g., three-dimensional) proximity of the sensor 146 to the point of incidence of the light/laser beam 134. Accordingly, with the light/laser beam 134 directed to the first location 52A of the target site, it should be understood that a strength of the photodiode signal generated by the sensor 146 may increase as a distance between the distal end 144 of the medical instrument 140 and the target site decreases as the sensor 146 may detect the light/laser beam 132 in a relatively close proximity.

It should be further understood that a strength (e.g., intensity variation) of the photodiode signal generated by the sensor 146 may decrease as a distance between the distal end 144 of the medical instrument 140 and the target site increases, as the sensor 146 may detect the light/laser beam 132 in a relatively further proximity. Although the sensor 146 in embodiments described herein includes a photodiode or CCD that is configured to generate a feedback in response to detecting the light/laser beam 132 in the form of a photodiode signal, it should be appreciated that various other suitable sensors and/or forms of feedback may be generated by a sensor on the medical instrument 140 without departing from a scope of this disclosure.

In some embodiments, the medical instrument 140 may include a processor and memory similar to the processor 104 and the memory 106 of the image processing device 102 shown and described above. In this instance, the processor of the medical instrument 140, when executing target identification logic stored on the memory of the medical instrument 140, may provide for autonomous steering of the medical instrument 140 relative to the first location 52A of the target site by tracking the light/laser beam 134 with the sensor 146. In other embodiments, the medical instrument 140 may be manually navigated to the first location 52A of the target site by a user of the medical system 100 by visually tracking a position of the distal end 144 relative to the first location 52A via a user interface display (not shown). In this instance, a user may visually navigate the distal end 144 of the medical instrument 140 toward the visual identifier generated by the light/laser beam 132. By way of illustrative example only, the distal end 144 of the medical instrument 140 may be displayed on a user interface display by a visual identifier, such as, for example, crosshairs superimposed on the user interface display that are indicative of a position of the distal end 144. Further, the feedback generated by the sensor 146 may be utilized in addition to and/or in lieu of the user interface display for manually steering the medical instrument 140 toward the first location 52A of the target site.

In some instances, the medical device 110 of the medical system 100 may move, intentionally and/or inadvertently, relative to the target site during a procedure as the medical instrument 140 moves toward the target site at step 212. Such movements may occur due to difficulties in maintaining the medical device 110 stable during a procedure. In this instance, a position of the target site (e.g., the ampulla of Vater 22) relative to the tip 122 of the shaft 120 and/or the distal end 144 of the medical instrument 140 may be modified and/or vary relative to an initial corresponding position between the target site and the medical device 110. Accordingly, the image data 109 initially obtained by the medical system 100 at step 206 may include inaccuracies and/or deficiencies in providing a current location of the target site (e.g., the ampulla of Vater 22). As a result, continued movement of the distal end 144 of the medical instrument 140 toward the first location 52A, as initially determined by the processor 104 of the imaging processing device 102 at step 208, may not allow a user of the medical system 100 to adequately access the target site.

At step 214 and referring to FIG. 5C, in response to the processor 104 of the image processing device 102 detecting a movement of the medical device 110 relative to the target site (e.g., the ampulla of Vater 22), the processor 104 may execute the target identification logic 108 to actuate the imaging device 130 to obtain updated image data 109 of the target site. In some embodiments, the processor 104 of the image processing device 102, when executing the target identification logic 108, may be configured to determine whether the medical device 110 has moved relative to the target site by periodically capturing images with the imaging device 130 for comparison to the image data 109 stored in the memory 106 at step 206. Accordingly, movement of the medical device 110 relative to the target site may be based on determining that a positional variance between the first location 52A and a detected position of the target site is equal to or greater than a preprogrammed threshold (e.g., a millimeter(s), a micrometer(s), a nanometer(s), etc.).

In this instance, upon determining that a recorded position of the first location 52A varies relative to a detected position of the target site via the periodically-captured images, the processor 104 of the image processing system 102 repeats steps 206, 208, 210, and 212 of the method 200 described above. The processor 104 executes the target identification logic 108 to capture images (e.g., image data 109) of the target site at step 206, determine a second location 52B of the target site (e.g., the ampulla of Vater 22) at step 208, and mark the second location 52B with the light/laser beam 134 at step 210. It should be understood that the method 200 performs these steps substantially similar to those shown and described above to facilitate locating the target site with the medical system 100 in accordance with the new, second location 52B of the target site.

In other embodiments, the image processing device 102 of the medical system 100 may be communicatively coupled to a remote station (not shown) for purposes of dynamically updating the target identification logic 108 stored on the memory 106. By way of illustrative example, the image processing device 102 may be operable to receive neural network data from a remote station (e.g., a computer server), such as, for example, via a wired and/or wireless connection. The neural network data received by the imaging processing device 102 may include supplemental image data 109, similar to the image data 109 shown and described above, recorded from a plurality of prior procedures, devices, systems, etc. Such image data may be from a plurality of different patients, acquired over time, of the same or similar patient anatomy. The supplemental image data 109 may be stored in the memory 106 and utilized by the processor 104 of the image processing device 102 to artificially determine and/or identify common physical properties and/or characteristics of one or more target sites, such as, for example, the ampulla of Vater 22 within the small intestine 18, the ampulla duct opening 22 of the common bile duct 20, etc.

In the embodiment, the processor 104 of the image processing device 102, when executing the machine-readable instructions of the target identification logic 108, may reference the supplemental image data 109 when analyzing the image data 109 captured by the imaging device 130 of the medical device 110 to determine the first location 52A of the target site (e.g., the ampulla of Vater 22 within the small intestine 18). Accordingly, it should be appreciated that the supplemental image data 109 may facilitate determining a coordinate position of a target site relative to the medical device 110 during a procedure by providing the image processing device 102 additional data for artificial learning of a size, shape, and/or configuration of similar target sites.

Each of the aforementioned devices, assemblies, and methods may be used to detect, mark and track a location of a target site. By providing a medical assembly, a user may accurately interact with a patient's tissue using artificial intelligence software in an image processing device during a procedure, allowing a user to reduce overall procedure time, increase efficiency of procedures, and avoid unnecessary harm to a patient's body caused by lack of control over a motion and positioning of a medical device when accessing target tissue of a patient.

It will be apparent to those skilled in the art that various modifications and variations may be made in the disclosed devices and methods without departing from the scope of the disclosure. It should be appreciated that the disclosed devices may include various suitable computer systems and/or computing units incorporating a plurality of hardware components, such as, for example, a processor and non-transitory computer-readable medium, that allow the devices to perform one or more operations during a procedure in accordance with those described herein. Other aspects of the disclosure will be apparent to those skilled in the art from consideration of the specification and practice of the features disclosed herein. It is intended that the specification and examples be considered as exemplary only.

We claim:

1. A medical system, comprising:
   a medical device including:
      an imaging device configured to capture images of a target site, wherein a location of the target site is determined based on the images; and
      a light source configured to direct a light onto the location of the target site;
   a sensor movably disposed within a lumen of the medical device, wherein the sensor is configured to detect the light on the target site; and
   a processor and non-transitory computer readable medium storing instructions,
   wherein the medical device is configured to receive the instructions, wherein the sensor is movable toward the target site in response to (i) the sensor receiving the instructions or (ii) the sensor detecting the light at the target site.

2. The medical system of claim 1, wherein the instructions stored in the non-transitory computer readable medium causes the processor to:
   detect a change in location of the imaging device relative to the target site; and
   determine the location of the target site relative to the imaging device,
   wherein, in response to detecting a change in location of the imaging device relative to the target site and determining the location of the target site relative to the imaging device, the light is redirected to the location of the target site.

3. The medical system of claim 2, wherein the processor is configured to detect the change in location of the imaging device relative to the target site based on images periodically captured by the imaging device; and
   wherein the processor is configured to compare the location of the target site to an original location of the target site to determine a positional variance.

4. The medical system of claim 3, wherein the processor is configured to determine whether the positional variance exceeds a preprogrammed threshold.

5. The medical system of claim 1, wherein the light source includes a source to generate a laser beam.

6. The medical system of claim 1, wherein the imaging device includes a camera.

7. The medical system of claim 1, wherein the sensor includes at least one of a photodetector, a photodiode, and a charged coupled device (CCD).

8. The medical system of claim 7, wherein the sensor is configured to generate a photodiode signal in response to detecting the light at the target site.

9. The medical system of claim 8, wherein a strength of the photodiode signal generated by the sensor includes a greater intensity when the sensor is positioned at a first distance from the light, and includes a smaller intensity when the sensor is positioned at a second distance from the light; and
   wherein the first distance is less than the second distance.

10. The medical system of claim 9, wherein the medical device includes a mirror configured to reflect the light generated by the light source toward the location of the target site.

11. The medical system of claim 10, wherein the mirror is configured to move to redirect the light toward the location of the target site in response to the processor detecting a change in location of the imaging device relative to the target site.

12. The medical system of claim 11, wherein the mirror includes a micro-mirror (MEMs mirror) configured to reflect the light along two axes.

13. The medical system of claim 12, wherein the mirror is positioned adjacent to the light source on the medical device.

14. The medical system of claim 1, wherein the processor is configured to generate a visual identifier along the images captured by the imaging device indicative of the location of the target site.

15. The medical system of claim 1, wherein the light source is disposed on a distal end of the medical device.

16. A medical system comprising:
   a medical device including:
      an imaging device configured to capture images of a target site; and
      a light source configured to direct a light onto the target site; and
   a medical instrument movably disposed within a working channel of the medical device, wherein the medical instrument is movable relative to the medical device, the medical instrument including a sensor configured to detect the light on the target site, wherein the medical instrument is movable toward the target site in response to the sensor detecting the light on the target site.

17. The medical system of claim 16, further comprising a processor configured to detect movement of the medical device relative to the target site based on images captured by the imaging device; and wherein the light source is configured to redirect the light based on the detected movement of the medical device.

18. The medical system of claim 16, wherein the medical device is an endoscope or duodenoscope, and the medical instrument is a catheter.

19. A method of moving a medical instrument toward a target site, the method comprising:
   delivering a medical system to a target site, the medical system comprising the medical instrument movably disposed within a medical device;
   capturing images of the target site with an imaging device of the medical device, wherein a first location of the target site is determined based on the images;
   transmitting a light to the first location by a light source;
   detecting the light at the first location by a sensor of the medical instrument; and
   moving the medical instrument relative to the medical device toward the target site based on the sensor detecting the light at the first location.

20. The method of claim 19, wherein in response to detecting movement of the medical instrument toward the target site, the method further comprises:
   capturing images of the target site with the imaging device to determine a second location of the target site;

redirecting the light from the light source to the second location; and moving the medical instrument toward the target site based on the sensor detecting the light at the second location.

\* \* \* \* \*